(12) United States Patent
Kassab

(10) Patent No.: US 8,099,161 B2
(45) Date of Patent: Jan. 17, 2012

(54) SYSTEMS AND METHODS FOR DETERMINING VESSEL COMPLIANCE

(75) Inventor: Ghassan S. Kassab, Zionsville, IN (US)

(73) Assignee: DTherapeutics, LLC, Zionsville, IN (US)

( * ) Notice: Subject to any disclaimer, the term of this patent is extended or adjusted under 35 U.S.C. 154(b) by 156 days.

(21) Appl. No.: 12/426,225

(22) Filed: Apr. 18, 2009

(65) Prior Publication Data

US 2009/0216133 A1 Aug. 27, 2009

Related U.S. Application Data

(60) Continuation of application No. 12/426,033, filed on Apr. 17, 2009, which is a continuation-in-part of application No. 12/098,242, filed on Apr. 4, 2008, which is a continuation-in-part of application No. 11/891,981, filed on Aug. 14, 2007, which is a division of application No. 10/782,149, filed on Feb. 19, 2004, now Pat. No. 7,454,244.

(60) Provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.
*A61B 5/05* (2006.01)
(52) U.S. Cl. ..................................................... 600/547
(58) Field of Classification Search .................. 600/547, 600/506, 505, 526, 587, 481, 486, 454, 561; 606/192, 194, 198; 128/898; 424/439; 623/1.11, 623/1.15, 23.7
See application file for complete search history.

(56) References Cited

U.S. PATENT DOCUMENTS 3,896,373 A 7/1975 Zelby
4,587,975 A 5/1986 Salo et al.
(Continued)

FOREIGN PATENT DOCUMENTS

EP 1 025 805 A1 8/2000
(Continued)

OTHER PUBLICATIONS

Tozzi et al, Systolic Axial Artery Length Reduction: an Overlooked Phenomenon in vivo, Am J Physiol Heart Circ Physiol, 280: H2300-H2305, 2001.*
(Continued)

*Primary Examiner* — Brian Szmal
(74) *Attorney, Agent, or Firm* — Ice Miller LLP

(57) ABSTRACT

The disclosure of the present application provides for systems and methods for determining a phasic change in a vessel and vessel compliance. In at least one exemplary method for determining a phasic change in a vessel, the method comprises the steps of introducing a device into a site within a vessel, operating the device in connection with two or more fluid injections in the vessel to obtain two or more conductance values, calculating a parallel conductance value and a total conductance value, and calculating a phasic change in at least one vessel parameter based in part upon the calculated parallel conductance value and the calculated total conductance value. In an exemplary method for determining vessel compliance, the method comprises, in part, the steps of calculating a first vessel parameter and a second vessel parameter based on at least two conductance values, calculating a change in vessel parameter based upon the first and second vessel parameters, and calculating vessel compliance based upon the relationship between the change in vessel parameter and a change in pressure during a cardiac cycle.

19 Claims, 13 Drawing Sheets

U.S. PATENT DOCUMENTS

| | | |
|---|---|---|
| 4,840,182 A | 6/1989 | Carlson |
| 5,058,583 A | 10/1991 | Geddes |
| 5,125,410 A | 6/1992 | Misono et al. |
| 5,233,994 A | 8/1993 | Shmulewitz |
| 5,366,443 A | 11/1994 | Eggers et al. |
| 5,453,576 A | 9/1995 | Krivitski |
| 5,665,103 A | 9/1997 | Lafontaine et al. |
| 5,971,933 A | 10/1999 | Schlueter |
| 6,112,115 A | 8/2000 | Feldman |
| 6,165,977 A | 12/2000 | Mochly-Rosen |
| 6,187,744 B1 | 2/2001 | Rooney |
| 6,191,136 B1 | 2/2001 | Marban |
| 6,270,493 B1 | 8/2001 | Lalonde et al. |
| 6,325,762 B1 | 12/2001 | Tjin |
| 6,354,999 B1 | 3/2002 | Dgany et al. |
| 6,360,123 B1 | 3/2002 | Kimchi |
| 6,398,738 B1 | 6/2002 | Millar |
| 6,406,422 B1 | 6/2002 | Landesberg |
| 6,471,656 B1 | 10/2002 | Shalman et al. |
| 6,494,832 B1 | 12/2002 | Feldman |
| 6,511,413 B2 | 1/2003 | Landesberg |
| 6,545,678 B1 | 4/2003 | Ohazama |
| 6,569,862 B1 | 5/2003 | Marban |
| 6,666,828 B2 * | 12/2003 | Greco et al. ............ 600/561 |
| 6,926,674 B2 | 8/2005 | Tenerz et al. |
| 7,141,019 B2 | 11/2006 | Pearlman |
| 7,169,107 B2 | 1/2007 | Jersey-Willuhn et al. |
| 7,189,208 B1 | 3/2007 | Beatty et al. |
| 7,236,820 B2 | 6/2007 | Mabary et al. |
| 7,326,241 B2 | 2/2008 | Jang |
| 2002/0049488 A1 * | 4/2002 | Boneau ............ 623/1.11 |
| 2003/0013986 A1 | 1/2003 | Saadat |
| 2004/0116816 A1 * | 6/2004 | Tenerz et al. ............ 600/486 |

FOREIGN PATENT DOCUMENTS

| | | |
|---|---|---|
| WO | WO 98/35611 A1 | 8/1998 |
| WO | WO 02/19905 | 3/2002 |
| WO | WO 02/085442 A1 | 10/2002 |
| WO | WO 03/092495 A1 | 11/2003 |

OTHER PUBLICATIONS

PCT/US04/04828, PCT Search Report and Written Opinion dated Jul. 6, 2005.

PCT/US06/05985, PCT Search Report and Written Opinion dated Aug. 8, 2007.

Supplementary European Search Report for EP Application Serial No. EP 04 71 2383 to Electro-Cat, LLC, dated Aug. 6, 2007.

Hoekstein and Inbar, "Cardiac Stroke Volume Estimation from Two Electrodes Electrical Impedance Measurements," Technion Department of Electrical Engineering Publication EE PUB No. 911, Feb. 1994.

L. Kornet, J.R.C. Jansen, E.J. Gussenhoven, M.R. Hardeman, A.P.G. Hoeks and A. Versprille, "Conductamce Method for the Measurement of Cross-Sectional Areas of the Aorta," Annals of Biomedical Engineering, vol. 27, pp. 141.150, 1999.

Douglas A. Hettrick, Joespeh Battocletti, James Ackmann, and David C. Warltier, "Finite Element Model Determination of Correction Factors Used for Measurement of Aorta Diameter via Conductance," Annals of Biomedical Engineering, vol. 27, pp. 151-159, 1999.

Douglas A. Hettrick, Joseph Battocletti, James Ackmann, John Linehan,a nd David C. Waritier, "In Vivo Measurement of Real-Time Aortic Segmental Volume Using the Conductance Catheter," Annals of Biomedical Engineering, vol. 26, pp. 431-440, 1998.

* cited by examiner

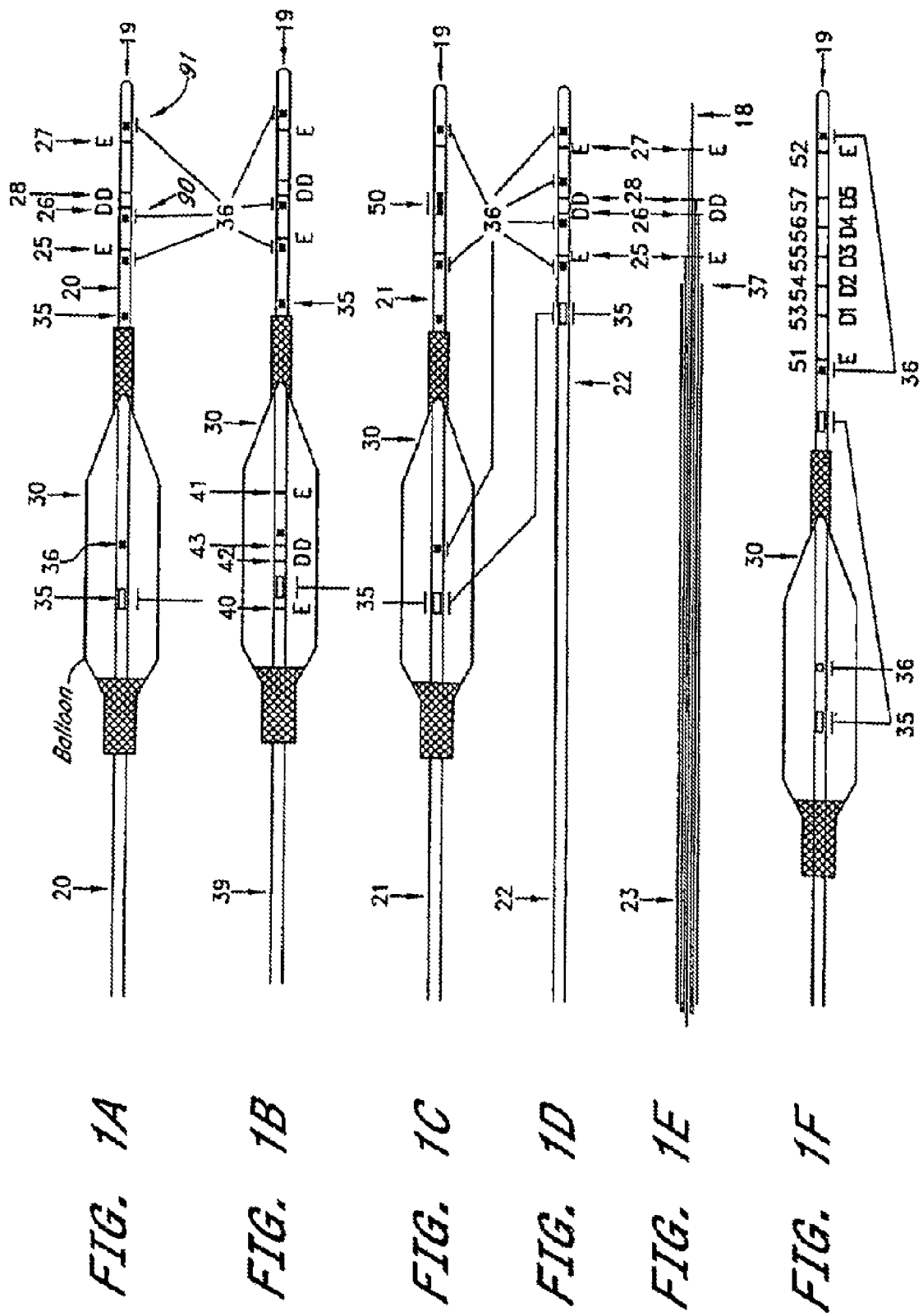

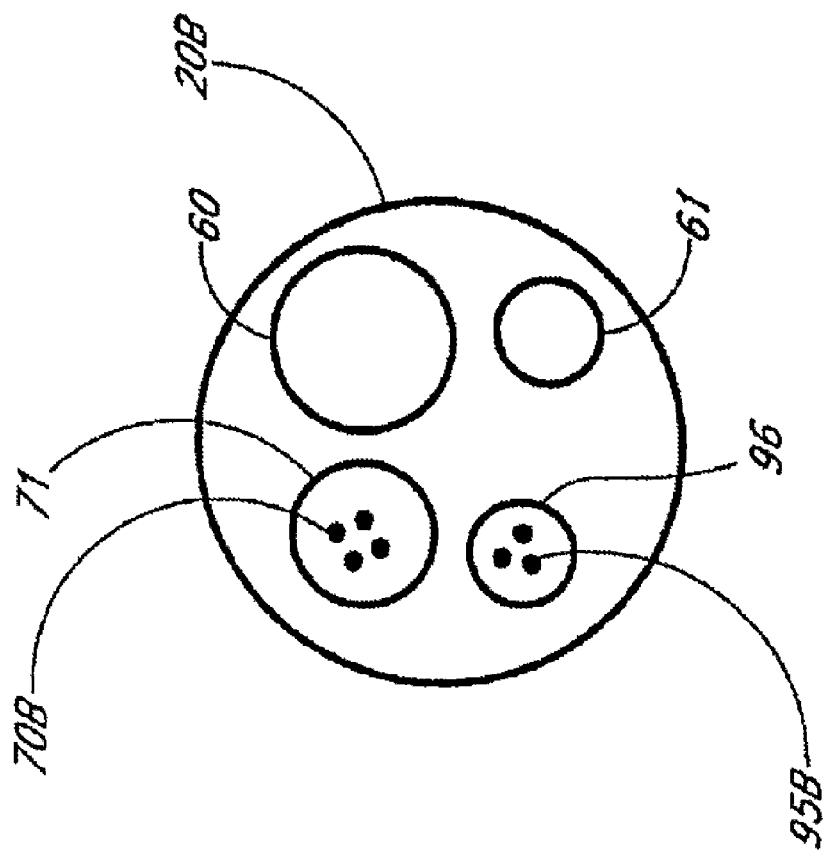
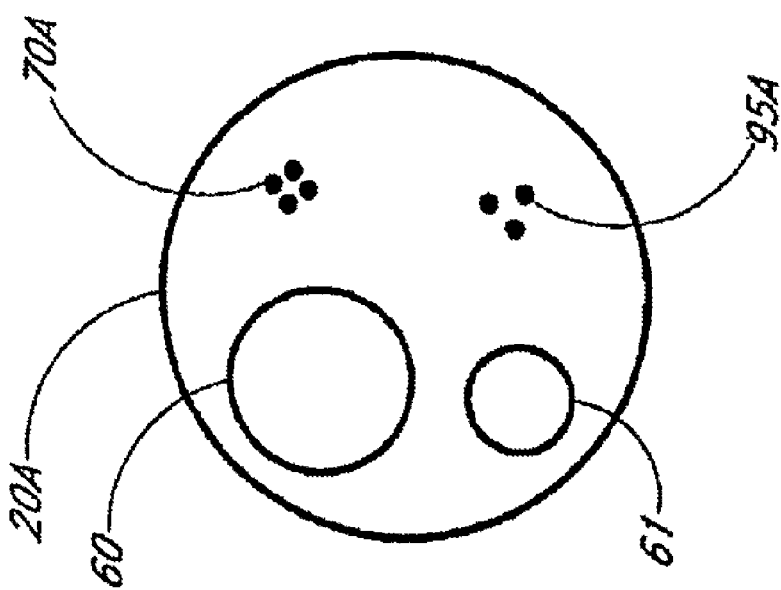

envelope data peak-peak of voltage at the detection electrodes

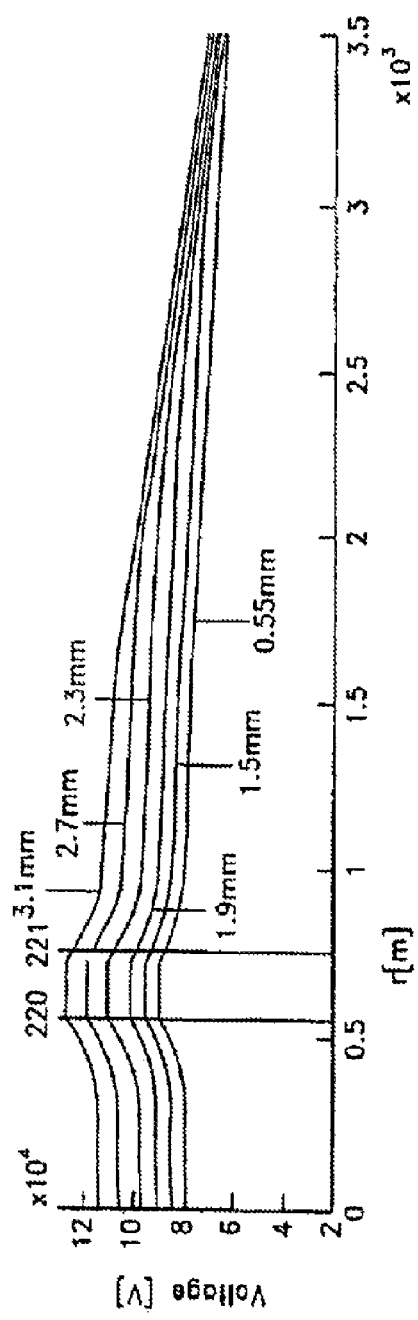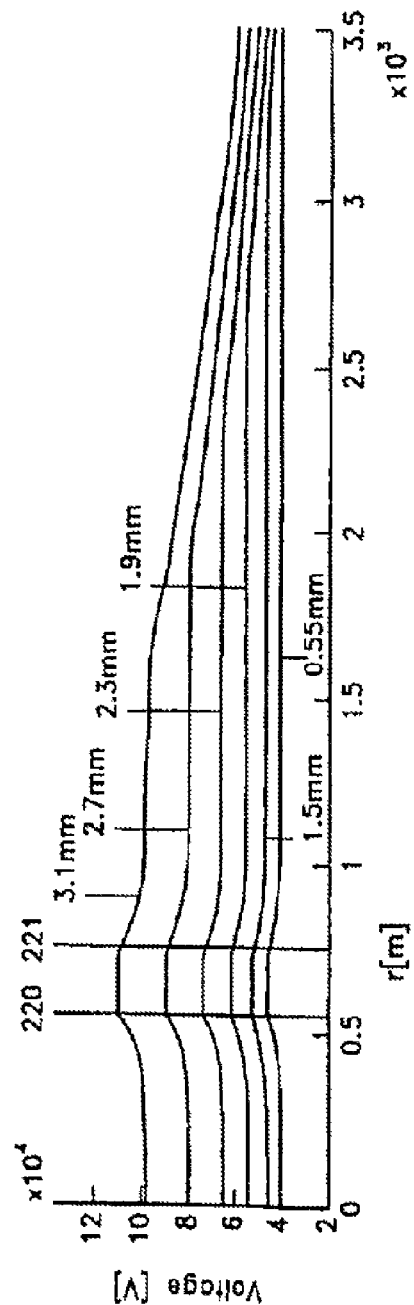

SYSTEMS AND METHODS FOR DETERMINING VESSEL COMPLIANCE

PRIORITY

This U.S. patent application is a continuation application of, and claims priority to, U.S. patent application Ser. No. 12/426,033, filed Apr. 17, 2009, which is a continuation-in-part application of, and claims priority to, U.S. patent application Ser. No. 12/098,242, filed Apr. 4, 2008, which is a continuation-in-part application of, and claims priority to, U.S. patent application Ser. No. 11/891,981, filed Aug. 14, 2007, which is a divisional application of, and claims priority to, U.S. patent application Ser. No. 10/782,149, filed Feb. 19, 2004, which issued as U.S. Pat. No. 7,454,244 on Nov. 18, 2008, which claims priority to U.S. Provisional Patent Application Ser. No. 60/449,266, filed Feb. 21, 2003, to U.S. Provisional Patent Application Ser. No. 60/493,145, filed Aug. 7, 2003, and to U.S. Provisional Patent Application Ser. No. 60/502,139, filed Sep. 11, 2003. The contents of each of these applications are hereby incorporated by reference in their entirety into this disclosure.

BACKGROUND

The disclosure of the present application relates generally to medical diagnostics and treatment equipment, and in particular, to devices, systems, and methods for measuring luminal cross-sectional area of blood vessels, heart valves and other hollow visceral organs. In addition, the disclosure of the present application relates generally to systems and methods for determining a phasic change in a vessel and vessel compliance.

Coronary Heart Disease

Coronary heart disease is caused by atherosclerotic narrowing of the coronary arteries. It is likely to produce angina pectoris, heart attack or both. Coronary heart disease caused 466,101 deaths in USA in 1997 and is the single leading cause of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the Stent Restenosis Study (STRESS) trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ, area, or space within a body. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angio-graphically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 cm$^2$, an area 0.75-1.0 cm$^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 cm$^2$ per year; the average rate of change is 0.12 cm$^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR), Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

BRIEF SUMMARY

The disclosure of the present application provides for systems and methods for determining a phasic change in a vessel and vessel compliance. In at least one embodiment of a method for determining a phasic change in a vessel of the present disclosure, the method comprises the steps of introducing a device into a site within a vessel, the device comprising a pair of excitation electrodes positioned along a portion of the device and a pair of detection electrodes positioned along a portion of the device, the pair of detection electrodes comprising two detection electrodes having a known distance from one another, the pair of detection electrodes physically positioned in between the pair of excitation electrodes along a portion of the device, operating the device in connection with two or more fluid injections in the vessel at or near the site to obtain two or more conductance values, calculating at least one parallel conductance value and at least one total conductance value at or near the site based upon at least two of the two or more conductance values, and calculating a phasic change in the at least one vessel parameter based upon the known distance of the two detection electrodes from one another, the calculated at least one parallel conductance value, and the calculated at least one total conductance value. In various embodiments, the at least one vessel parameter comprises at least one vessel diameter and/or at least one vessel cross-sectional area. In another embodiment, the step of calculating a phasic change in the at least one vessel parameter is further based upon a mean conductivity of a fluid present within the vessel.

In at least one embodiment of a method for determining a phasic change in a vessel of the present disclosure, the fluid present within the vessel comprises blood. In an exemplary embodiment, the step of calculating a phasic change in the at least one vessel parameter considers a constant representing a mean conductivity of a fluid present within the vessel, and in at least one embodiment, the constant may vary by no more than 10%.

In at least one embodiment of a method for determining a phasic change in a vessel of the present disclosure, the method further comprises the step of determining the extent of vessel disease based upon the calculated phasic change in the at least one vessel parameter. In various embodiments, the extent of vessel disease is determined to be relatively low if the calculated phasic change in the at least one vessel parameter is relatively high, is determined to be relatively high if the calculated phasic change in the at least one vessel parameter is relatively low, and/or is determined to include vessel calcification if the calculated phasic change in the at least one vessel parameter is zero. In an exemplary embodiment, the extent of vessel disease includes a vessel disease selected from the group consisting of atherosclerosis, vessel calcification, degenerative calcific disease, congenital heart disease, rheumatic disease, and coronary artery disease.

In at least one embodiment of a method for determining a phasic change in a vessel of the present disclosure, the calculated at least one parallel conductance value used in the step of calculating a phasic change in the at least one vessel parameter is a mean parallel conductance value. In another embodiment, the site comprises a site selected from the group consisting of a body lumen, a body vessel, a biliary tract, and an esophagus. In yet another embodiment, the step of providing electrical current flow for a period of time to the site through the device. In an additional embodiment, the device comprises a device selected from the group consisting of an impedance catheter, a guide catheter, a guide wire, and a pressure wire.

In at least one embodiment of a method for determining a phasic change in a vessel of the present disclosure, the device used further comprises an inflatable balloon positioned along a portion of the device, and the method further comprises the step of inflating the balloon to breakup materials causing stenosis at the site. In an additional embodiment, the device further comprises a stent positioned over the balloon, the stent capable of being distended to a desired size and implanted into the site, and the method further comprises the steps of distending the stent by inflating the balloon, and releasing and implanting the stent into the site. In at least one embodiment, the balloon is inflated using a fluid, and the method further comprises the steps of providing electrical current to the fluid filling the balloon at various degrees of balloon distension, measuring a conductance of the fluid inside the balloon, and calculating a cross-sectional area of the balloon lumen.

In at least one embodiment of a method for determining a phasic change in a vessel of the present disclosure, the device used further comprises a stent positioned along a portion of the device, the stent capable of being distended to a desired size and implanted into the site. In an exemplary embodiment, the method further comprising the steps of positioning the stent at or near the site, distending the stent, and releasing and implanting the stent into the site. In at least one embodiment, the two or more conductance values are retrieved by a data acquisition and processing system operably connected to the device, and the data acquisition and processing system is operable to calculate a phasic change in the at least one vessel parameter. In another embodiment, the device comprises at least one suction/infusion port in communication with at least one lumen of the device, whereby the two or more fluid injections occur via the at least one suction/infusion port.

In at least one embodiment of a method for determining a phasic change in a vessel of the present disclosure, the device used comprises a catheter having a lumen, a proximal end, and a distal end, and the pair of excitation electrodes and the pair of detection electrodes are positioned along a portion of the device at or near the distal end of the device. In another embodiment, the pair of excitation electrodes and the pair of detection electrodes have insulated electrical wire connections that run through the lumen and proximal end of the catheter. In at least one embodiment, the calculated phasic change is indicative of a phasic change throughout a cardiac cycle.

In at least one embodiment of a method for determining a phasic change in a vessel of the present disclosure, the method comprises the step of introducing a device into a site within a vessel, the device comprising a catheter having a lumen, a proximal end, and a distal end, a pair of excitation electrodes positioned along a portion of the device at or near the distal end of the device, and a pair of detection electrodes positioned along a portion of the device at or near the distal end of the device, the pair of detection electrodes comprising two detection electrodes having a known distance from one another, the pair of detection electrodes physically positioned in between the pair of excitation electrodes along a portion of the device, operating the device in connection with two or more fluid injections in the vessel at or near the site to obtain two or more conductance values, wherein the two or more conductance values are retrieved by a data acquisition and processing system operably connected to the device, calculating at least one parallel conductance value and at least one total conductance value at or near the site based upon at least two of the two or more conductance values, calculating a phasic change in the at least one vessel parameter using the data acquisition and processing system based upon the known distance of the two detection electrodes from one another, the calculated at least one parallel conductance value, and the calculated at least one total conductance value, and determining the extent of vessel disease based upon the calculated phasic change in the at least one vessel parameter, wherein the extent of vessel disease is determined to be relatively low if the calculated phasic change in the at least one vessel parameter is relatively high, and wherein the extent of vessel disease is determined to be relatively high if the calculated phasic change in the at least one vessel parameter is relatively low.

In at least one method for determining vessel compliance of the present disclosure, the method comprises the steps of introducing a device into a site within a vessel, the device comprising a pair of excitation electrodes positioned along a portion of the device, and a pair of detection electrodes positioned along a portion of the device, the pair of detection electrodes comprising two detection electrodes having a known distance from one another, the pair of detection electrodes physically positioned in between the pair of excitation electrodes, operating the device in connection with two or more fluid injections in the vessel at or near the site to obtain two or more conductance values, each of the two or more fluid injections having a known conductivity, calculating a first vessel parameter of the site based on at least two of the two or more conductance values and the conductivities of at least two of the two or more fluid injections, calculating a second vessel parameter of the site based on at least two of the two or more conductance values and the conductivities of at least two of the two or more fluid injections, calculating a change in vessel parameter based upon the first vessel parameter and the second vessel parameter, and calculating vessel compliance based upon the relationship between the change in vessel parameter and a change in pressure during a cardiac cycle. In another embodiment, the method further comprises the step of determining the extent of vessel disease based upon the calculated vessel compliance. In various embodiments, the extent of vessel disease is determined to be relatively low if the calculated vessel compliance is relatively high, is determined to be relatively high if the calculated vessel compliance is relatively low, an/or is determined to include vessel calcification if the calculated vessel compliance is zero. In at least one embodiment, the extent of vessel disease includes a vessel disease selected from the group consisting of atherosclerosis, vessel calcification, degenerative calcific disease, congenital heart disease, rheumatic disease, and coronary artery disease.

In at least one method for determining vessel compliance of the present disclosure, the two or more conductance values are retrieved by a data acquisition and processing system operably connected to the device, and the data acquisition and processing system is operable to calculate vessel compliance.

In another embodiment, the change in pressure during a cardiac cycle has a constant value for a patient. In various embodiments, the first vessel parameter and the second vessel parameter each comprise a vessel diameter, and the change in vessel parameter comprises a change in vessel diameter, or the first vessel parameter and the second vessel parameter each comprise a vessel cross-sectional area, and the change in vessel parameter comprises a change in vessel cross-sectional area.

In at least one method for determining vessel compliance of the present disclosure, the method further comprises the step of calculating an index of compliance based in part upon a difference between the first vessel parameter and the second vessel parameter divided by the first vessel parameter. In an exemplary embodiment, the first vessel parameter comprises a first vessel systolic diameter, the second vessel parameter comprises a second vessel diastolic diameter, and the first vessel systolic diameter and the second vessel diastolic diameter are representative of a single vessel. In another embodiment, the first vessel parameter comprises a first vessel systolic cross-sectional area, the second vessel parameter comprises a second vessel diastolic cross-sectional area, and the first vessel systolic cross-sectional area and the second vessel diastolic cross-sectional area are representative of a single vessel.

In at least one method for determining vessel compliance of the present disclosure, the device used comprises a device selected from the group consisting of an impedance catheter, a guide catheter, a guide wire, and a pressure wire. In at least one embodiment, the device further comprises an inflatable balloon positioned along a portion of the device, and the method further comprises the step of inflating the balloon to breakup materials causing stenosis at the site. In another embodiment, the device further comprises a stent positioned over the balloon, the stent capable of being distended to a desired size and implanted into the site, and the method further comprises the steps of distending the stent by inflating the balloon, and releasing and implanting the stent into the site. In an additional embodiment, the balloon is inflated using a fluid, and the method further comprises the steps of providing electrical current to the fluid filling the balloon at various degrees of balloon distension, measuring a conductance of the fluid inside the balloon, and calculating a cross-sectional area of the balloon lumen. In yet an additional embodiment, the device used comprises at least one suction/infusion port in communication with at least one lumen of the device, whereby the two or more fluid injections occur via the at least one suction/infusion port.

In an at least one method for determining vessel compliance of the present disclosure, the method comprises the steps of introducing a device into a site within a vessel, the device comprising a pair of excitation electrodes and a pair of detection electrodes positioned therebetween, operating the device to obtain two or more conductance values, calculating a change in cross-sectional area based in part upon the two or more conductance values, and calculating vessel compliance based upon the relationship between the change in cross-sectional area and a change in pressure during a cardiac cycle.

In at least one embodiment of a system for determining a phasic change in a vessel of the present disclosure, the system comprises a device capable of acquiring conductance data, the device comprising a pair of excitation electrodes positioned along a portion of the device and a pair of detection electrodes positioned along a portion of the device, the pair of detection electrodes comprising two detection electrodes having a known distance from one another, the pair of detection electrodes physically positioned in between the pair of excitation electrodes along a portion of the device, an injection source for injecting one or more solutions through the device to a target site, a current source for providing current to the device, and a data acquisition and processing system that receives conductance data from the device, wherein the data acquisition and processing system is operable to calculate a phasic change in the at least one vessel parameter based upon the known distance of the two detection electrodes from one another, and a calculated at least one parallel conductance value and a calculated at least one total conductance value, each value calculated based upon the conductance data acquired from the device.

In at least one embodiment of a system for determining vessel compliance of the present disclosure, the system comprises a device capable of acquiring conductance data, the device comprising a pair of excitation electrodes positioned along a portion of the device and a pair of detection electrodes positioned along a portion of the device, the pair of detection electrodes comprising two detection electrodes having a known distance from one another, the pair of detection electrodes physically positioned in between the pair of excitation electrodes along a portion of the device, an injection source for injecting one or more solutions through the device to a target site, a current source for providing current to the device and a data acquisition and processing system that receives conductance data from the device, wherein the data acquisition and processing system is operable to calculate vessel compliance based upon a calculated change in vessel parameter based upon a calculated first vessel parameter and a calculated second vessel parameter, the calculated first vessel parameter and a calculated second vessel parameter calculated based upon the conductance data acquired from the device, and a calculated relationship between the calculated change in vessel parameter and a change in pressure during a cardiac cycle.

BRIEF DESCRIPTION OF THE DRAWINGS

FIG. 1A illustrates a balloon catheter having impedance measuring electrodes supported in front of the stenting balloon;

FIG. 1B illustrates a balloon catheter having impedance measuring electrodes within and in front of the balloon;

FIG. 1C illustrates a catheter having an ultrasound transducer within and in front of balloon;

FIG. 1D illustrates a catheter without a stenting balloon;

FIG. 1E illustrates a guide catheter with wire and impedance electrodes;

FIG. 1F illustrates a catheter with multiple detection electrodes;

FIG. 2A illustrates a catheter in cross-section proximal to the location of the sensors showing the leads embedded in the material of the probe;

FIG. 2B illustrates a catheter in cross-section proximal to the location of the sensors showing the leads run in separate lumens;

FIG. 8A illustrates the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site;

FIG. 8B illustrates the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site;

DETAILED DESCRIPTION

Figure 3:
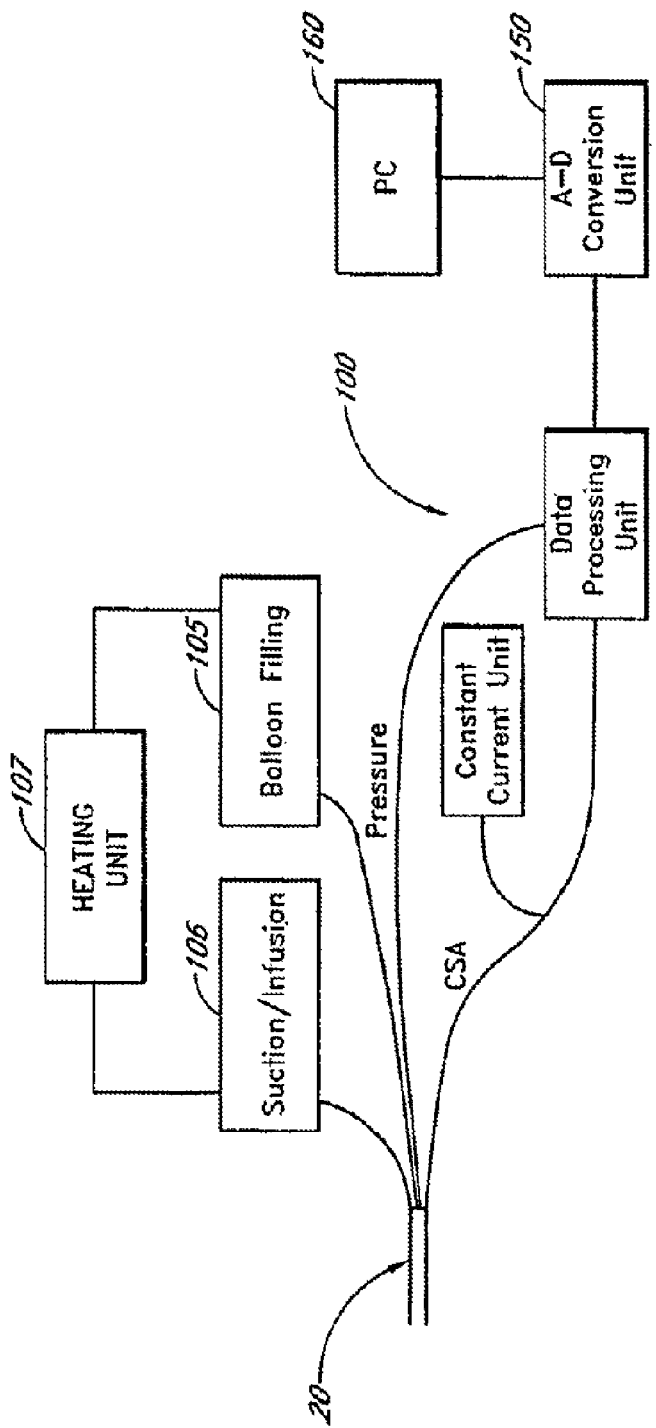
FIG. 3 is a schematic of one embodiment of the system showing a catheter carrying impedance measuring electrodes connected to the data acquisition equipment and excitation unit for the cross-sectional area measurement.

The disclosure of the present application provides devices, systems, and methods to obtain accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the disclosure of the present application overcome the problems associated with determination of the size (cross-sectional area) of luminal organs, such as, for example, in the coronary arteries, carotid, femoral, renal and iliac arteries, aorta, gastrointestinal tract, urethra and ureter. Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Catheter

Exemplary impedance or conductance catheters for use within the disclosure of the present application are illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes. It can be appreciated that catheters of various sizes and including electrodes positioned in various locations may be useful in accordance with the present disclosure.

In one approach, dimensions of a catheter to be used for any given application depend on the optimization of the potential field using finite element analysis described below. For small organs, or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In a preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C, and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27, and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, catheter 20 advantageously includes pressure port 90 and pressure port 91 proximal to or at the site of the cross-sectional measurement for evaluation of pressure gradients. As described below with reference to FIGS. 2A, 2B, and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27, and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56, and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C, the catheter 21 has one or more imaging or recording devices, such as, for example, ultrasound transducers 50 for cross-sectional area and wall thickness measurements. As shown in this embodiment, the transducers 50 are located near the distal tip 19 of the catheter 21.

FIG. 1D illustrates an embodiment of impedance catheter 22 without an angioplastic or stenting balloon. The catheter in this exemplary embodiment also possesses an infusion or injection port 35 located proximal relative to the excitation electrode 25 and pressure port 36.

With reference to the embodiment shown in FIG. 1E, the electrodes 25, 26, 27, and 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E, and 1F, the impedance catheter advantageously includes optional ports 35, 36, and 37 for suction of contents of the organ or infusion of fluid. The suction/infusion ports 35, 36, and 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter may contain an extra channel for insertion of a guide wire to stiffen the flexible catheter during the insertion or data recording. In yet another embodiment (not illustrated), the catheter may include a sensor for measurement of the flow of fluid in the body organ.

System for Determining Cross-Sectional Area and Pressure Gradient

The operation of the impedance catheter 20 is as follows: With reference to the embodiment shown in FIG. 1A for electrodes 25, 26, 27, and 28, conductance of current flow through the organ lumen and organ wall and surrounding tissue is parallel; i.e., $$G(z, t) = \frac{CSA(z, t) \cdot C_b}{L} + G_p(z, t) \qquad [1a]$$

where $G_p(z,t)$ is the effective conductance of the structure outside the bodily fluid (organ wall and surrounding tissue) at a given position, z, along the long axis of the organ at a given time, t, and $C_b$ is the electrical conductivity of the bodily fluid which for blood generally depends on the temperature, hematocrit and orientation and deformation of blood cells, and L is the distance between the detection electrodes. Equation [1a] can be rearranged to solve for cross sectional area CSA(t), with a correction factor, α, if the electric field is non-homogeneous, as $$CSA(z, t) = \frac{L}{\alpha C_b}[G(z, t) - G_p(z, t)] \quad [1b]$$

where α would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that α is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation [1a] allows the calculation of the electrical conductivity of blood in the presence of blood blow as $$C_b = \frac{L}{CSA(z, t)}[G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity, U. Equation [1b] can be expressed as $$CSA(U \cdot t, t) = \frac{L}{C_b}[G(U \cdot t, t) - G_p(U \cdot (t, t)] \quad [7]$$

where the axial position, z, is the product of catheter velocity, U, and time, t; i.e., z=U·t.

For the two injections, denoted by subscript "1" and subscript "2", respectively, different time points $T_1$, $T_2$, etc., may be considered such that equation [7] can be written as $$CSA_1(U \cdot T_1, t) = \frac{L}{C_1}[G_1(U \cdot T_1, t) - G_{p1}(U \cdot T_1, t)] \quad [8a]$$

$$CSA_1(U \cdot T_1, t) = \frac{L}{C_2}[G_2(U \cdot T_1, t) - G_{p1}(U \cdot T_1, t)] \quad [8b]$$

and $$CSA_2(U \cdot T_2, t) = \frac{L}{C_1}[G_1(U \cdot T_2, t) - G_{p2}(U \cdot T_2, t)] \quad [9a]$$

$$CSA_2(U \cdot T_2, t) = \frac{L}{C_2}[G_2(U \cdot T_2, t) - G_{p2}(U \cdot T_2, t)] \quad [9b]$$

and so on. Each set of equations [8a], [8b] and [9a], [9b], etc. can be solved for $CSA_1$, $G_{p1}$ and $CSA_2$, $G_{p2}$, respectively. Hence, the CSA at various time intervals may be measured and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a profile on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruct the CSA and $G_p$ along the length of the 2 cm segment, namely at 0 mm, 4 mm, 8 mm, 12 mm, 16 mm, and 20 mm.

Operation of the impedance catheter 39: With reference to the embodiment shown in FIG. 1B, the voltage difference between the detection electrodes 42 and 43 depends on the magnitude of the current, I, multiplied by the distance, D, between the detection electrodes and divided by the conductivity, C, of the fluid and the cross-sectional area, CSA, of the artery or other organs into which the catheter is introduced. Since the current, I, the distance, L, and the conductivity, C, normally can be regarded as calibration constants, an inverse relationship exists between the voltage difference and the CSA as shown by the following equations:

$$\Delta V = \frac{I \cdot L}{C \cdot CSA} \quad [10a]$$

or $$CSA = \frac{G \cdot L}{C} \quad [10b]$$

where G is conductance expressed as the ratio of current to voltage, I/ΔV. Equation [10] is identical to Equation [1b] if the parallel conductance through the vessel wall is neglected and surrounding tissue because the balloon material acts as an insulator. This is the cylindrical model on which the conductance method is used.

As described below with reference to FIGS. 2A, 2B, 3, 4, and 5, the excitation and detection electrodes are electrically connected to electrically conductive leads in the catheter for connecting the electrodes to the data acquisition system 100.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

With reference to FIG. 3, in one exemplary embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a constant current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The cross-sectional area, CSA, and parallel conductance, $G_p$, and other relevant measures such as distensibility, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying profile of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_w$ is the wall area of the organ and $C_w$ is the electrical conductivity through the wall. This equation can be solved for the wall $CSA_w$ as $$CSA_w = \frac{G_p \cdot L}{C_w} \quad [11b]$$

For a cylindrical organ, the wall thickness, h, can be expressed as $$h = \frac{CSA_w}{\pi D} \quad [12]$$

where D is the diameter of the vessel which can be determined from the circular CSA (D=$[4\, CSA/\pi]^{1/2}$).

When the CSA, pressure, wall thickness, and flow data are determined according to the embodiments outlined above, it is possible to compute the compliance (e.g., ΔCSA/ΔP), tension (e.g., P·r, where P and r are the intraluminal pressure and radius of a cylindrical organ), stress (e.g., P·r/h where h is the wall thickness of the cylindrical organ), strain (e.g., $(C-C_d)/C_d$ where C is the inner circumference and $C_d$ is the circumference in diastole) and wall shear stress (e.g., $4\mu Q/r^3$ where μ, Q and r are the fluid viscosity, flow rate and radius of the cylindrical organ, respectively, for a fully developed flow). These quantities can be used in assessing the mechanical characteristics of the system in health and disease.

Exemplary Method

In one approach, luminal cross-sectional area is measured by introducing a catheter from an exteriorly accessible opening (e.g., mouth, nose, or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD) artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance, G=I/V. The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a the sampling frequency of 75 KHz, with two channels—the current injected and the detected voltage, respectively. The current injected has a frequency of 5 KHz, so the voltage detected, modulated in amplitude by the impedance changing through the bolus injection will have a spectrum in the vicinity of 5 KHz.

Figure 4A:
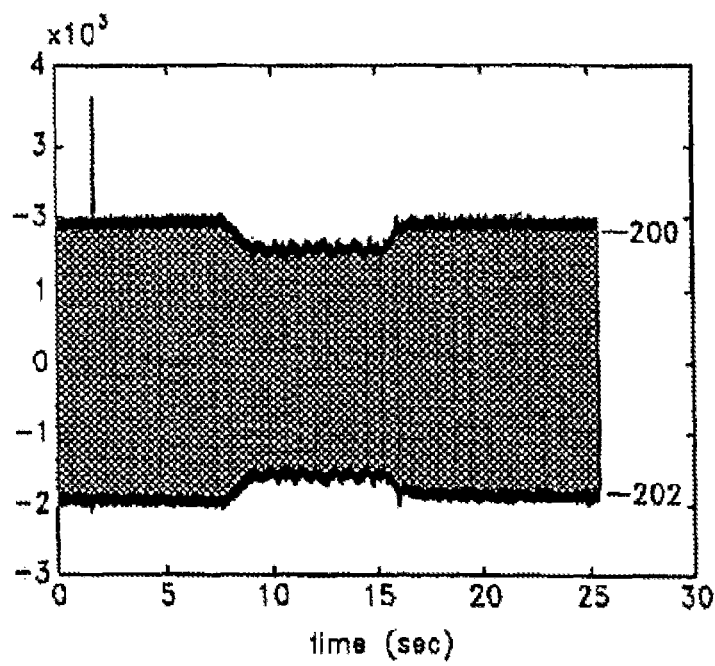
FIG. 4A show the detected filtered voltage drop as measured in the blood stream before and after injection of 1.5% NaCl solution.
Figure 4B:
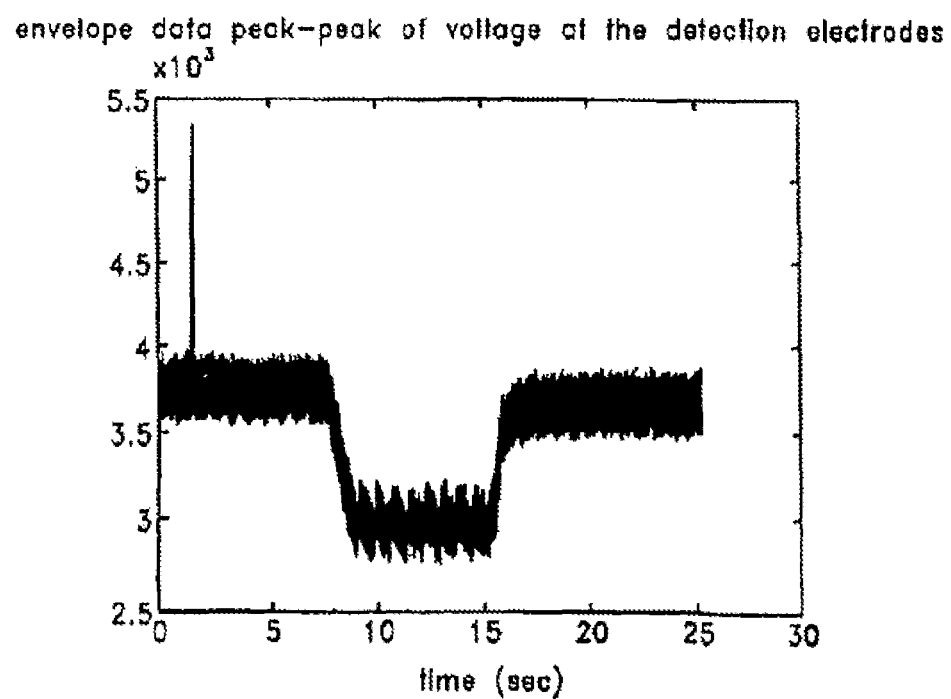
FIG. 4B shows the peak-to-peak envelope of the detected voltage shown in FIG. 4A.
Figure 5A:
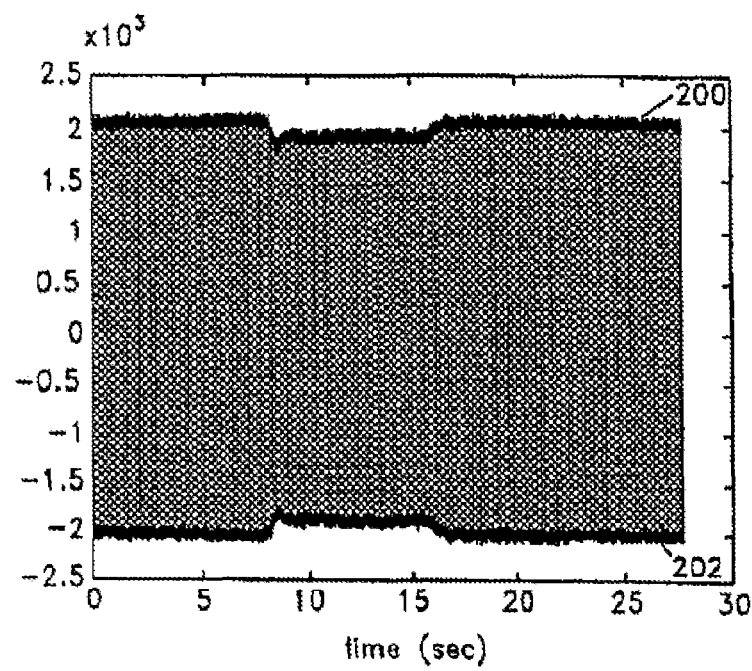
FIG. 5A show the detected filtered voltage drop as measured in the blood stream before and after injection of 0.5% NaCl solution.
Figure 5B:
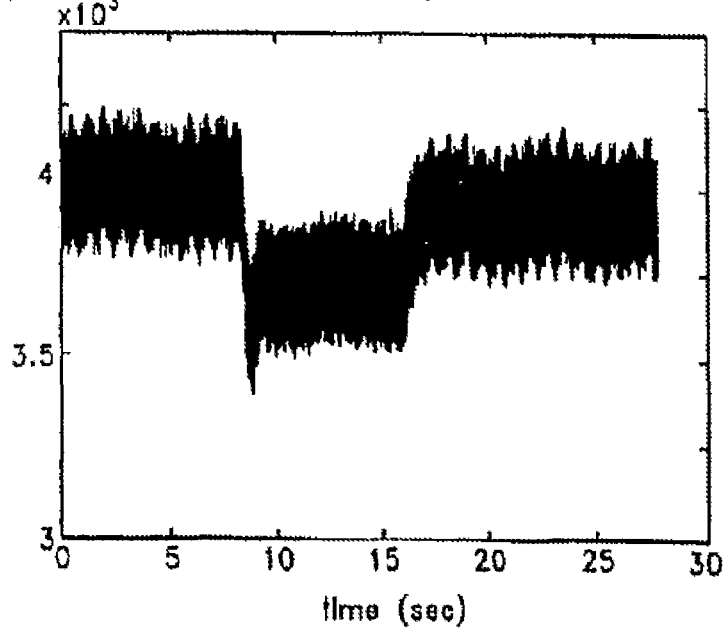
FIG. 5B shows the peak-to-peak envelope of the detected voltage shown in FIG. 5A.

With reference to FIG. 4A, there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B shows similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation [4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 mm² (3 mm in diameter) to 1.017 mm² (36 mm in diameter). If the conductivity of the solutions is obtained from a conductivity meter independent of the catheter, however, then the CSA of the catheter is generally added to the CSA computed from Equation [4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the CSA.

Exemplary Four-Injection Approach

In at least one method of the disclosure of the present application, a four-injection approach is provided. As previously disclosed herein, two injections provide the cross-sectional area, CSA, and parallel conductance, $G_p$, at a particular point.

In at least one approach, four injections are provided to determine parallel conductance at multiple points. In an exemplary study, four injections may be performed to determine a segment of 2-3 cm long or longer. In this study, two injections may be performed at the distal end of the segment, and two injections may be performed at the proximal end of the segment. The two injections may deliver, for example, a volume of 1.5% NaCl and a volume of 0.5% NaCl, at each end of the segment, noting that any number of solutions, volumes, and concentrations thereof suitable for such a study, or for the other studies contemplated by the disclosure of the present application, could be utilized. For example, solutions having different salinities can be introduced in various physiological saline solutions (PSS) or in a Kreb solution containing other ions such as potassium, sodium, etc. In this exemplary study, the first two injections (1.5% NaCl and 0.5% NaCl) may be made at the distal point of the segment, and the catheter system would then be pulled back to the proximal point of the segment, whereby two more injections (1.5% NaCl and 0.5% NaCl) may be made, with conductance values taken at the distal end and the proximal end of the segment used to determine the entire profile of the segment.

As referenced herein with respect to Equation [1a], conductance may be calculated taking into account cross-sectional area, electrical conductivity of a fluid, and effective conductance of a structure. When performing a study as described above, the two end points (proximal and distal ends of a segment) are clearly exact, and an intermediate profile between those two points can be derived based upon the analysis provided herein. Since the cross-sectional area, CSA, and parallel conductance at a point, $G_p$, are known at each of the two ends of a segment, the corresponding blood conductivity may be calculated:

$$G_{Total} = \frac{CSA \cdot C_b}{L} + G_p \quad [13]$$

where $G_{Total}$ is the total conductance (current divided by voltage), CSA is the cross-sectional area, $C_b$ is the blood conductivity, L is the detection electrode spacing on the catheter, and $G_p$ is the parallel conductance at a point. The mean of the two values may then be calculated based upon the foregoing.

A procedure as described above may be accomplished, for example, by performing the following steps:

Step 1: Calculate total conductance ($G_{Total}$, current divided by voltage, or I/V, where I is the current injected and V is the voltage recorded) for two ends (proximal and distal) of a segment.

Step 2: Calculate the Coeff ratio (cross-sectional area divided by total conductance, or CSA/$G_{Total}$) at the two ends of the segment.

Step 3: Linearly interpolate along the length of the pull back for the Coeff, so that the two ends of the segment have the same Coeffs calculated from Step 2 above.

Step 4: Calculate total conductance ($G_{Total}$) for the entire length of the pull back (distance between the two ends of the segment).

Step 5: At each point calculated in the pull back, multiply the total conductance ($G_{Total}$) times its respective Coeff. The product of this calculation is the cross-sectional area (CSA).

Step 6: Determine the diameter from the cross-sectional area (CSA) along the entire profile.

A mathematical explanation of the concept referenced in the procedure above is as follows. First, the equation governing the physics of electrical conductance has the following form:

$$G_{Total} = \frac{I}{V} = \frac{CSA \cdot \sigma}{L} + G_p \quad [14]$$

where $G_{Total}$ is the total conductance, I is the current, V is the voltage, CSA is the cross-sectional area, $\sigma$ is the conductivity of the fluid, L is the detection electrode spacing on the catheter, and $G_p$ is the parallel conductance at a point.

Experimentation as shown that parallel conductance ($G_p$) is linearly related to cross-sectional area, with a negative slope. For example, a larger CSA has a smaller $G_p$. As such, $G_p$ can be replaced with a linear function of CSA as follows:

$$G_{Total} = \frac{I}{V} = \frac{CSA \cdot \sigma}{L} + m \cdot CSA + b \quad [15]$$

where $G_{Total}$ is the total conductance, I is the current, V is the voltage, CSA is the cross-sectional area, σ is the conductivity of the fluid, L is the detection electrode spacing on the catheter, m is the slops, and b is the intercept as can be determined for a linear least square fit. This may be rearranged as follows:

$$G_{Total} = \left(\frac{\sigma}{L} + m\right) CSA + b \quad [16]$$

It is shown that total conductance ($G_{Total}$) is clearly linearly related to cross-sectional area (CSA). If the coefficient b is ignored (wherein b should be equal to zero if CSA is equal to zero), then we have the following:

$$\left(\frac{CSA}{G_{Total}}\right) = Coeff \quad [17]$$

The Coeff value at both ends of a segment can be found where the two injections are made, and those values may then be used to linearly interpolate across the profile. Once a Coeff value for every point in the pull back is determined, those Coeff values are multiplied by their respective $G_{Total}$ values to determine the CSA values along the profile, namely:

$$CSA = Coeff * G_{Total} \quad [18]$$
and $$Diameter = \sqrt{\frac{4 * CSA}{\pi}} \quad [19]$$

to determine a diameter.

Exemplary Three-Injection Approach

In at least one method of the disclosure of the present application, a three-injection approach to determine a profile as outlined above with respect to the four-injection approach is also provided. In at least one approach, three injections are provided, with two injections at the distal end of a segment, simultaneous withdrawal of one of the injection sources, and one injection at the proximal end of the segment.

In an exemplary study, the first two injections at the distal end may deliver, for example, a volume of 1.5% NaCl and a volume of 0.5% NaCl, noting that any number of solutions, volumes, and concentrations thereof suitable for such a study could be utilized. In this exemplary study, the first two injections (1.5% NaCl and 0.5% NaCl) may be made at the distal point of the segment, wherein the catheter system is simultaneously withdrawn with the injection of the 0.5% NaCl so that the 0.5% NaCl may also be used for the proximal end. These injections would then be followed by a 1.5% NaCl injection at the proximal end of the segment.

Advantages to this particular approach over the four-injection approach are that (1) the conductivity would be simplified as that of 0.5% rather than blood, and (2) there are only three injections required instead of four. However, the three-injection method also requires that a physician using a catheter system to perform such a procedure would be required to inject and pull back simultaneously. A physician comfortable with simultaneous injection and pull back may prefer the three-injection approach, while a physician not comfortable with simultaneous injection and pull back may prefer the four-injection approach. Either approach is possible using the algorithm provided herein.

Ex-Vivo and In-Vivo Validation of Algorithm

Studies were performed ex-vivo in in-vivo to validate the algorithm provided herein. The former was validated in a carotid artery with an artificial stenosis to compare the algorithm disclosed herein versus cast measurements for both for the two-injection method at several discrete points and the reconstructed profile. The latter validation was done in vivo in a coronary artery (LAD) where a comparison between LR (LumenRecon) and IVUS (intravascular) was made.

Ex-Vivo Validation of Algorithm

Figure 9:
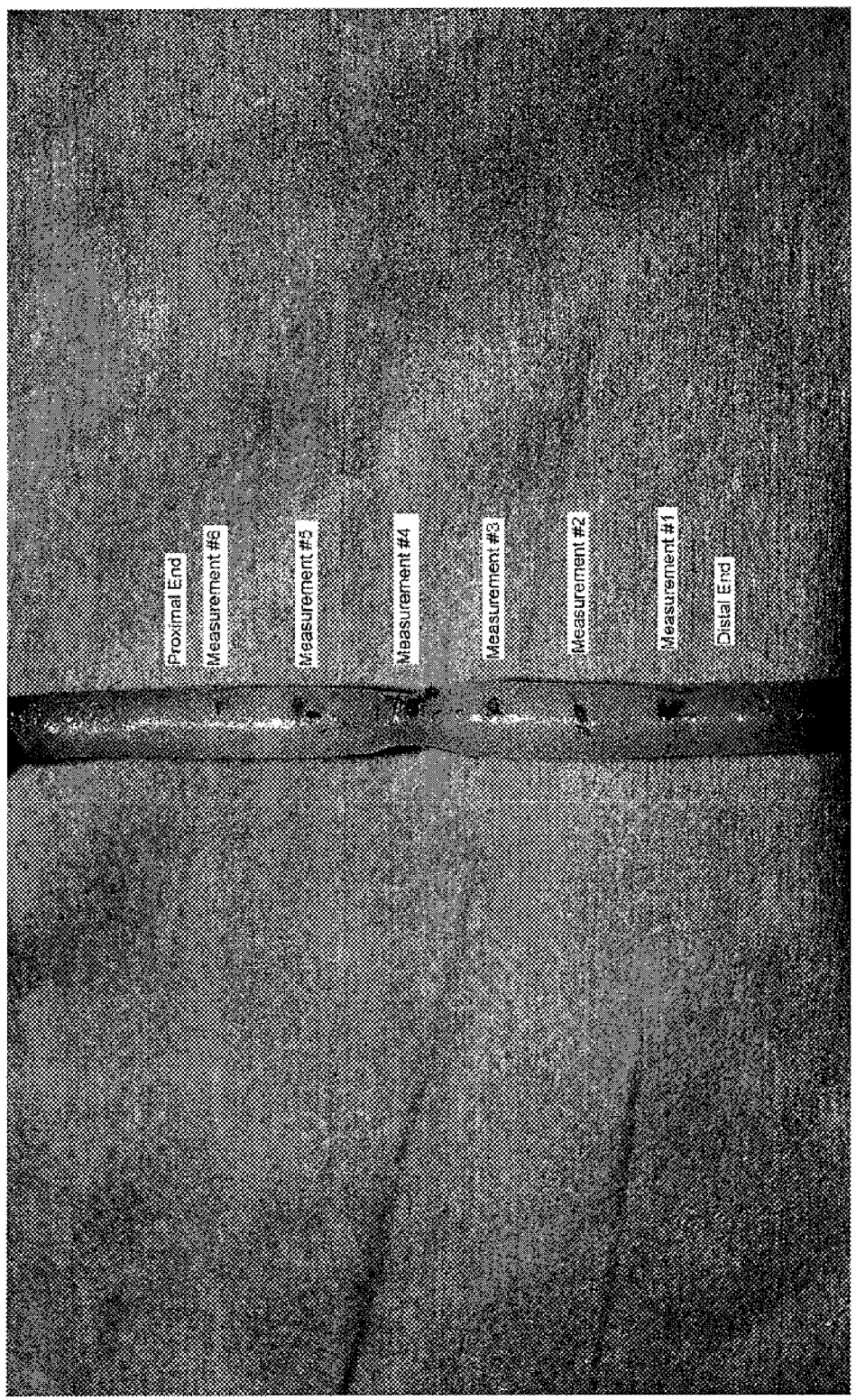
FIG. 9 shows a photograph of a segment of swine carotid artery used for performing ex-vivo validation of the algorithm of the present disclosure.

To validate the algorithm ex-vivo, a segment of a swine carotid artery was removed and mounted on a bench stand as shown in FIG. 9. A small portion of one end of the vessel was removed and used to create a stenosis around the vessel, which was accomplished by wrapping this piece of tissue around the middle of the vessel and shortening the piece of tissue using suture. A black indicator was used to mark the outside of the vessel at six locations along the length (length=3.23 cm). As shown in FIG. 9, the bottom portion of the vessel is the distal end, and black marks signify where LumenRecon measurements were made using a two-injection method of the present disclosure.

The LumenRecon system was calibrated using the 0.45% and 1.5% saline concentrations. A two-injection method according to the present disclosure was used to make single diameter measurements at the six locations along the length of the vessel. "Pull back" measurements were also made along the length of the vessel to create a continuous profile of the vessel diameter.

After the LumenRecon measurements were taken, a cast mold of the vessel was created. The diameter of the cast mold of the vessel was determined using microscopy. The cast measurements were taken at the six locations marked by the black indicator and at intermediate locations along the vessel.

Figure 10:
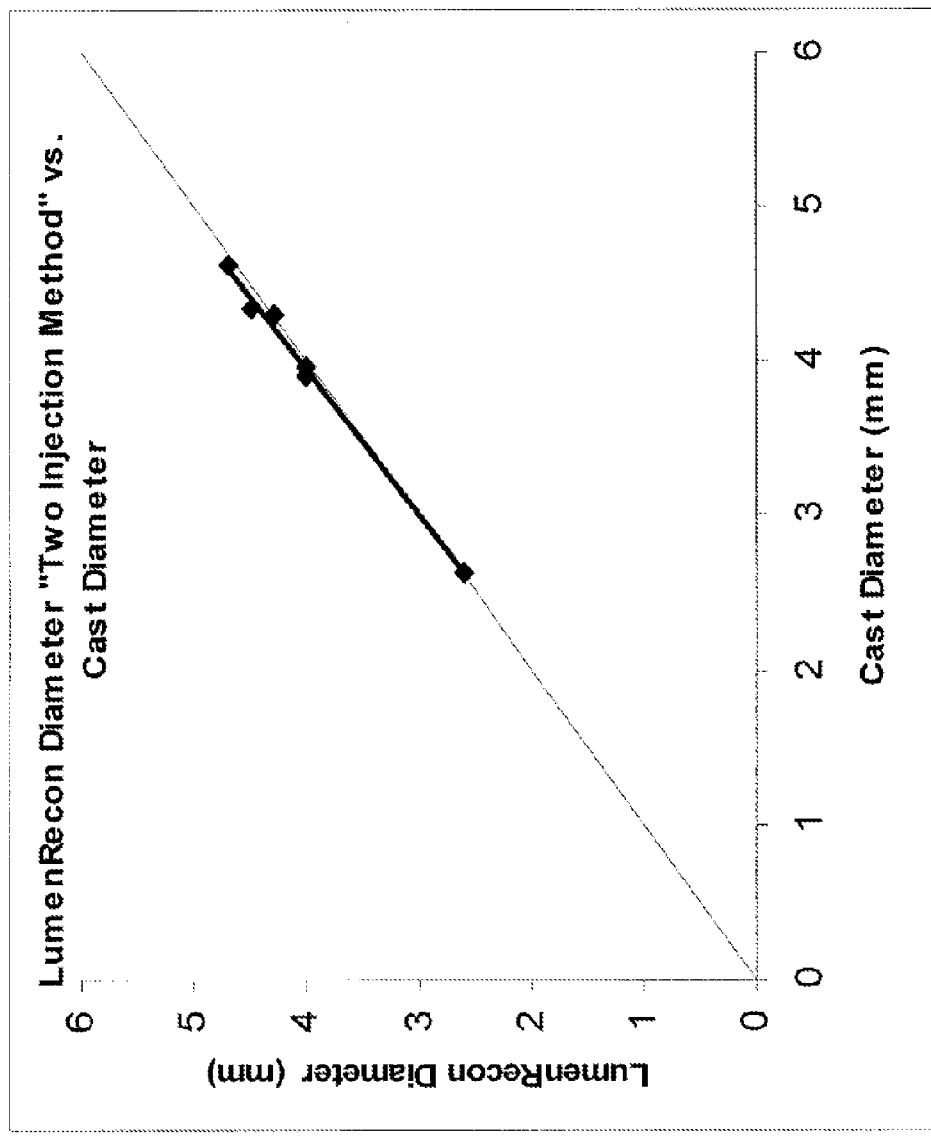
FIG. 10 shows ex-vivo data using a two-injection method of the present disclosure.
Figure 11:
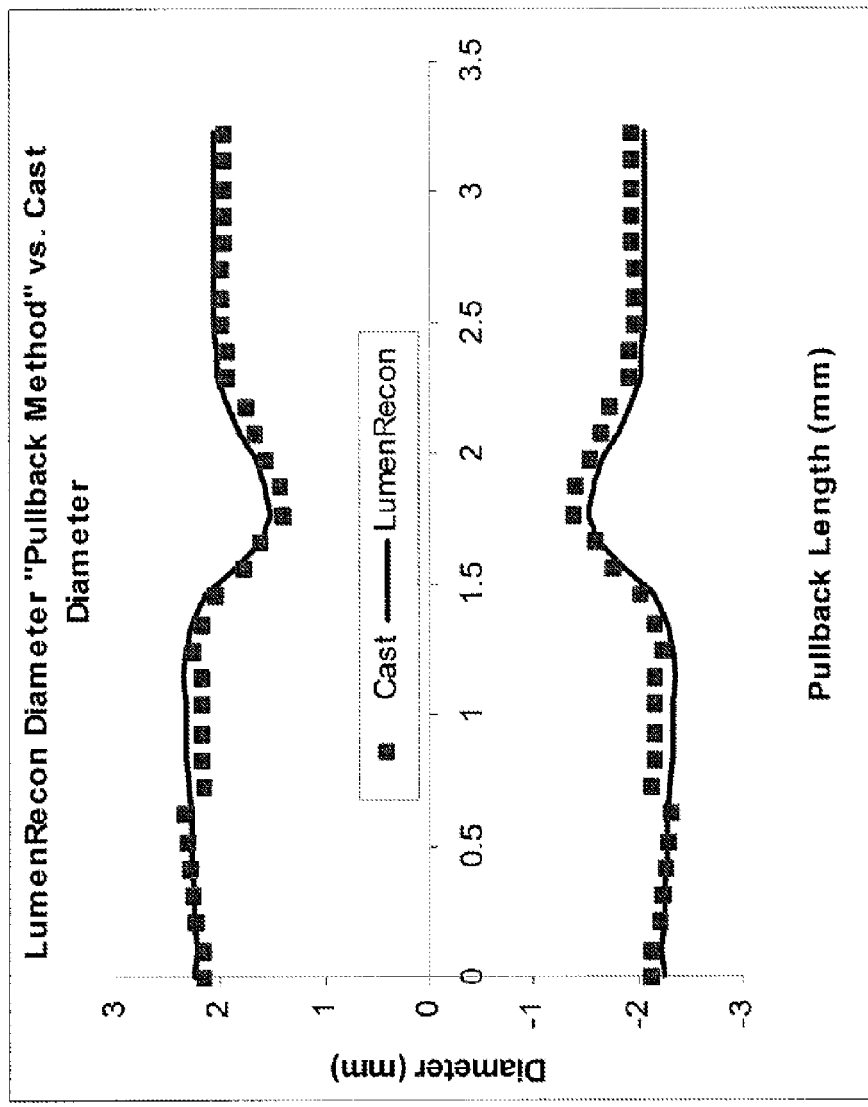
FIG. 11 shows ex-vivo data using a pull back method of the present disclosure.

The diameters from the LumenRecon two injection method and the pull back measurements were plotted against the cast measurements, respectively. FIG. 10 shows the data for the six locations using a two-injection method of the present disclosure, comparing the diameters calculated by the LumenRecon system to those measured from the cast mold of the vessel using microscopy. The least square fit of the data shows y=1.0599x−0.1805, $R^2$=0.9944. FIG. 11 shows a profile of data points (diameters) using a pull back method of the present disclosure, comparing the diameters calculated by the LumenRecon system to those measured from the cast mold of the vessel using microscopy.

In Vivo Validation

Figure 12:
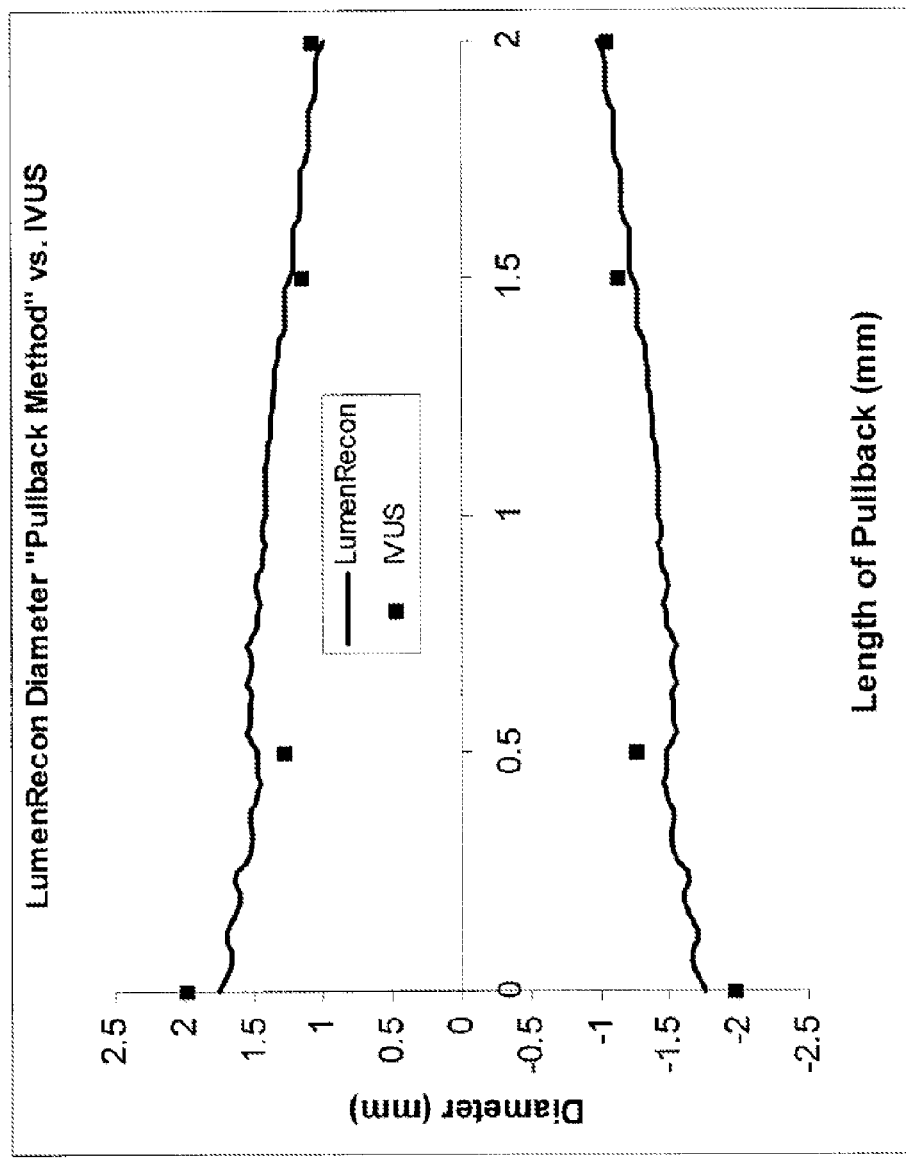
FIG. 12 shows in-vivo data using a two-injection method of the present disclosure as compared to the IVUS method.

The LumenRecon system was used to make measurements in the left anterior descending (LAD) coronary artery in an anesthetized swine. A two-injection method of the present disclosure was used to construct a profile which was compared to IVUS at four different locations along the profile. FIG. 12 shows the LumenRecon measurements plotted against the IVUS measurements, showing the measurements before and after the temperature correction. The temperature correction was incorporated into the calibration of the catheter. It was determined that a NaCl solution injected at room temperature (25° C.) reaches 30° C. when at the body site of measurement (39° C.). Hence, calibrations of fluid were made at 30° C. to account for the heating of the fluid during injection.

Phasic Changes of Vessel Lumen Area

As discussed above and herein, an exemplary two-injection method may provide the mean CSA and $G_p$ at any particular point. Equation [14], as described in detail above, provides the equation governing the physics of electrical conductance as applied to CSA, fluid conductivity, and parallel conductance. At a fixed spatial position in a vessel, the mean conductivity of blood, $\sigma_b$, can then be determined from Equation [14] as follows:

$$\overline{\sigma_b} = \frac{L}{\overline{CSA}}[G_{Total}(t) - \overline{G_p}] \quad [20]$$

wherein $\overline{\sigma_b}$ is the mean conductivity of blood, L is the detection electrode spacing on a catheter, $\overline{CSA}$ is the mean cross-sectional area, $G_{Total}(t)$ is the total conductance at a given time, and $\overline{G_p}$ is the mean parallel conductance. In at least one embodiment, and in a situation where only one parallel conductance value is known, the value of the parallel conductance value may be substituted in place of a mean parallel tissue conductance value.

As blood conductivity only varies by approximately ten percent (10%) through the cardiac cycle, blood conductivity, for the purposes described herein, may also be considered as a constant having a mean value. Hence, the phasic change of CSA (at any given location) during the cardiac cycle can be calculated by the following equation:

$$CSA(t) = \frac{L}{\overline{\sigma_b}}[G_{Total}(t) - \overline{G_p}] \quad [21]$$

wherein CSA(t) is the phasic change in cross-sectional area, L is the detection electrode spacing on a catheter, $\overline{\sigma_b}$ is the mean conductivity of blood, $G_{Total}(t)$ is the total conductance at a given time, and $\overline{G_p}$ is the mean parallel conductance.

Figure 13A:
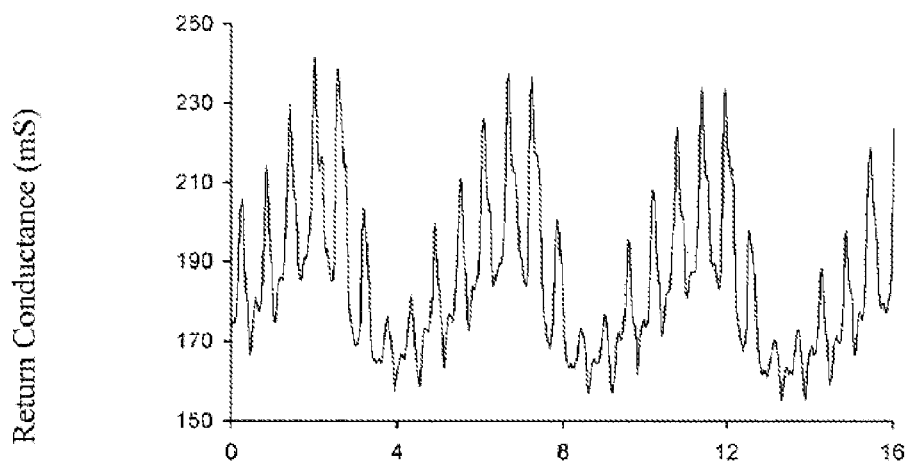
FIG. 13A shows phasic changes of total conductance showing cardiac and respiratory changes as referenced herein.

The temporal changes of CSA, or diameter derived therefrom as referenced herein, can be determined from the phasic changes of total conductance. For example, conductance data as shown in FIG. 13A, can be converted to CSA or diameter of the artery as outlined above. FIG. 13A shows the phasic changes of total conductance showing cardiac and respiratory changes, with the narrow tall peaks representing detected heart rate, and the sinusoidal wave (approximately three and one half wavelengths shown) represents respiratory changes (inhalation and exhalation).

Figure 13B:
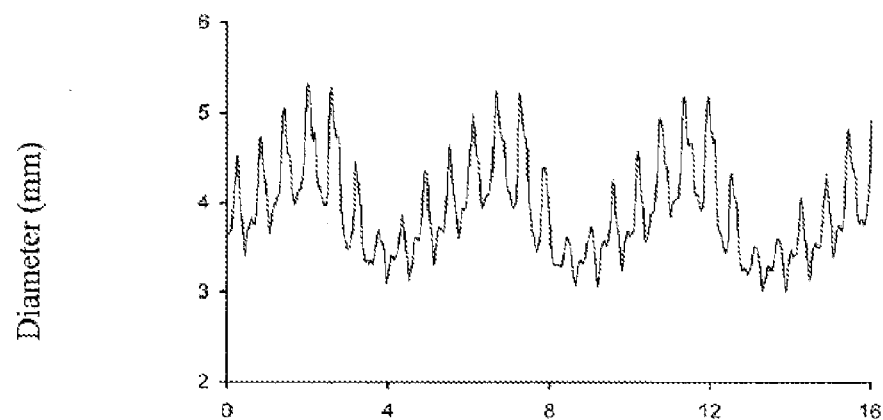
FIG. 13B shows the phasic changes of diameter for an exemplary normal coronary artery.
Figure 13C:
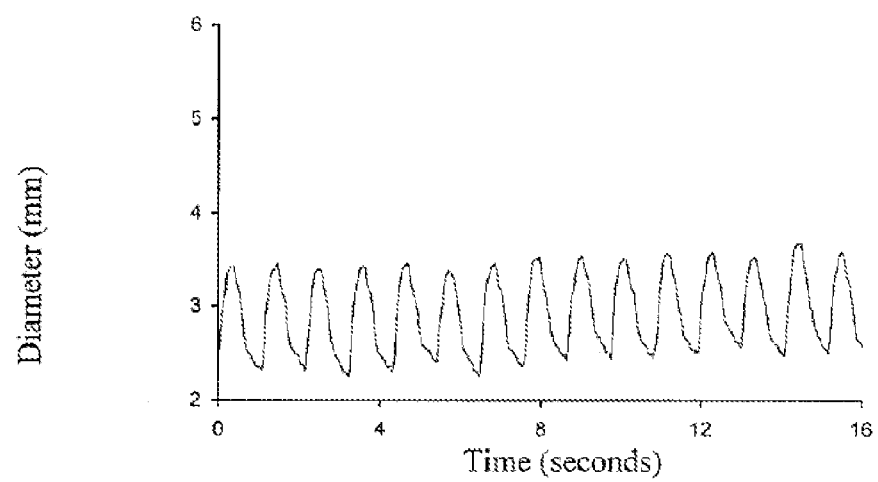
FIG. 13C shows the phasic changes of diameter for an exemplary atherosclerotic coronary artery.

The phasic changes of diameters of a normal coronary artery (FIG. 13B) or an atherosclerotic coronary artery (FIG. 13C) are shown throughout several cardiac cycles. FIG. 13B shows the phasic changes of a "normal" blood vessel (without any sort of stenosis or lesion) having a similar profile to the profile shown in FIG. 13A. The cardiac as well as respiratory changes of coronary diameter are apparent for the normal animal. FIG. 13C shows the same parameters (changes in diameter of a vessel over time) shown in FIG. 13B, but instead of a "normal" vessel, the results are reflective of a diseased (atherosclerotic) vessel. As shown in FIG. 13C, only changes in vessel diameter due to the cardiac cycle are shown, noting that respiration has no visible impact on vessel diameter of this exemplary diseased vessel (noting that the respiratory changes for the conductance data vanish in the atherosclerotic animals).

The phasic changes of blood vessel shown in FIGS. 13A-13C have clinical importance. A healthy vessel, for example, will show significant changes in vessel diameter through the cardiac cycle as shown in FIG. 13B. A calcified vessel, on the other hand, will show no changes in diameter through the cardiac cycle as shown in FIG. 13C. A decrease in compliance (or increase in stiffness) of vessels has been well established with vascular disease.

The compliance of a vessel determined by the change of CSA per change of pressure through the cardiac cycle is described as follows:

$$C = \Delta CSA/\Delta P \quad [22]$$

wherein C is vessel compliance, $\Delta CSA$ is the change of cross-sectional area, and $\Delta P$ is the change in pressure through the cardiac cycle. Alternatively, since the $\Delta P$ is relatively constant for various patients, an index of compliance can be expressed as $$\%\Delta CSA = (CSA_{systolic} - CSA_{diastolic})/CSA_{diastolic} \times 100 \quad [23]$$

wherein % $\Delta CSA$ is the index of compliance, $CSA_{systolic}$ is the cross-sectional area of a vessel during systole, and $CSA_{diastolic}$ is the cross-sectional area of a vessel during diastole. Similarly, Equations [22] and [23] can be expressed in terms of diameter, wherein values for cross-sectional area are replaced with values for diameter.

Such relations, as described herein, can be used to determine a phasic change or the compliance of the vessel and hence the degree of vascular disease. For example, if a vessel is deemed to have relatively low compliance or have a relatively low calculated phasic change in diameter or cross-sectional area, the extent of vessel disease may be determined to be relatively high. Conversely, and for example, if a vessel is deemed to have relatively high compliance or have a relatively high calculated phasic change in diameter or cross-sectional area, the extent of vessel disease may be determined to be relatively low. Currently, no other imaging method, including, but not limited to, angiography or IVUS, has the temporal resolution to provide the phasic changes throughout the cardiac cycle in real-time as referenced herein.

Figure 6:
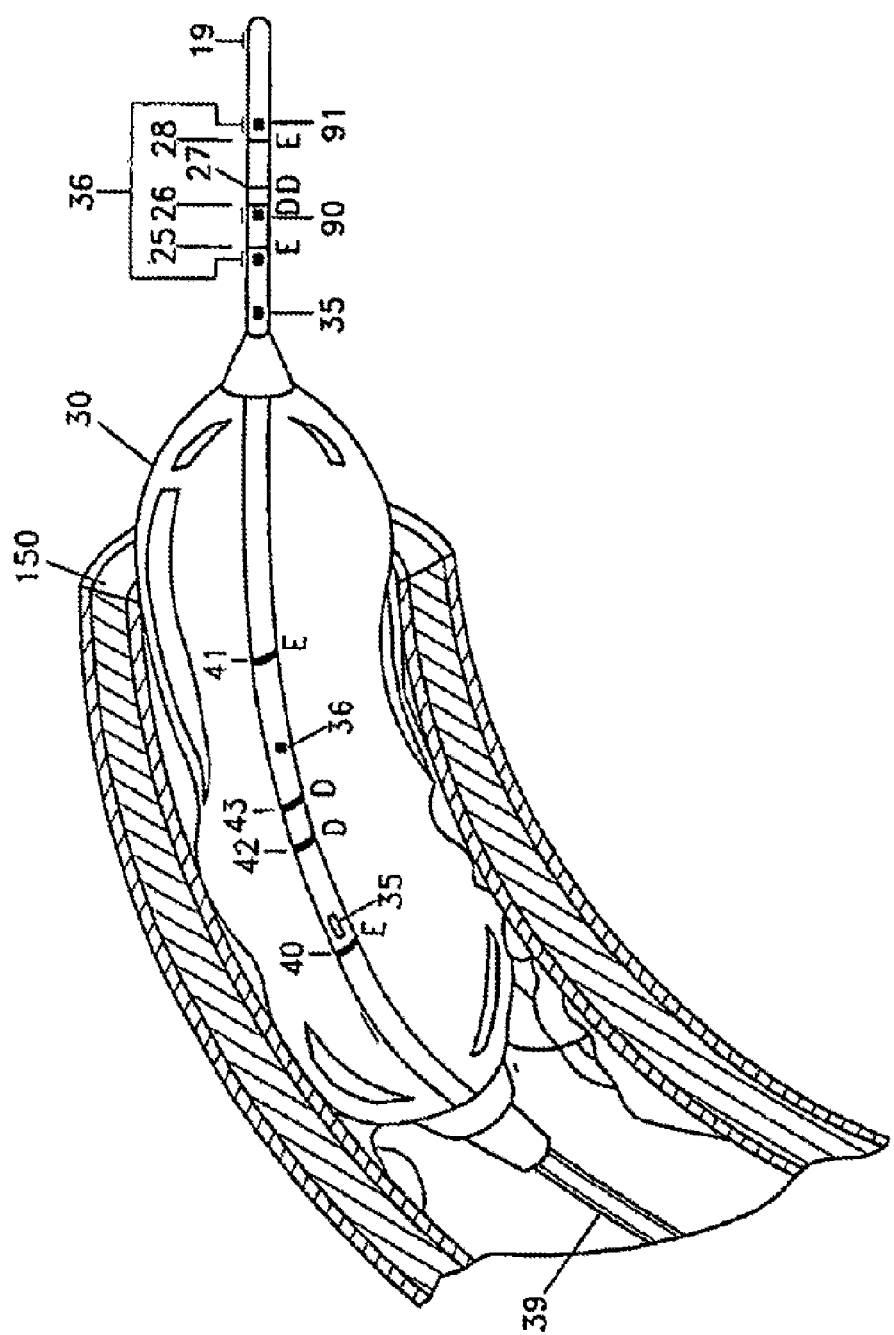
FIG. 6 illustrates balloon distension of the lumen of the coronary artery.
Figure 7:
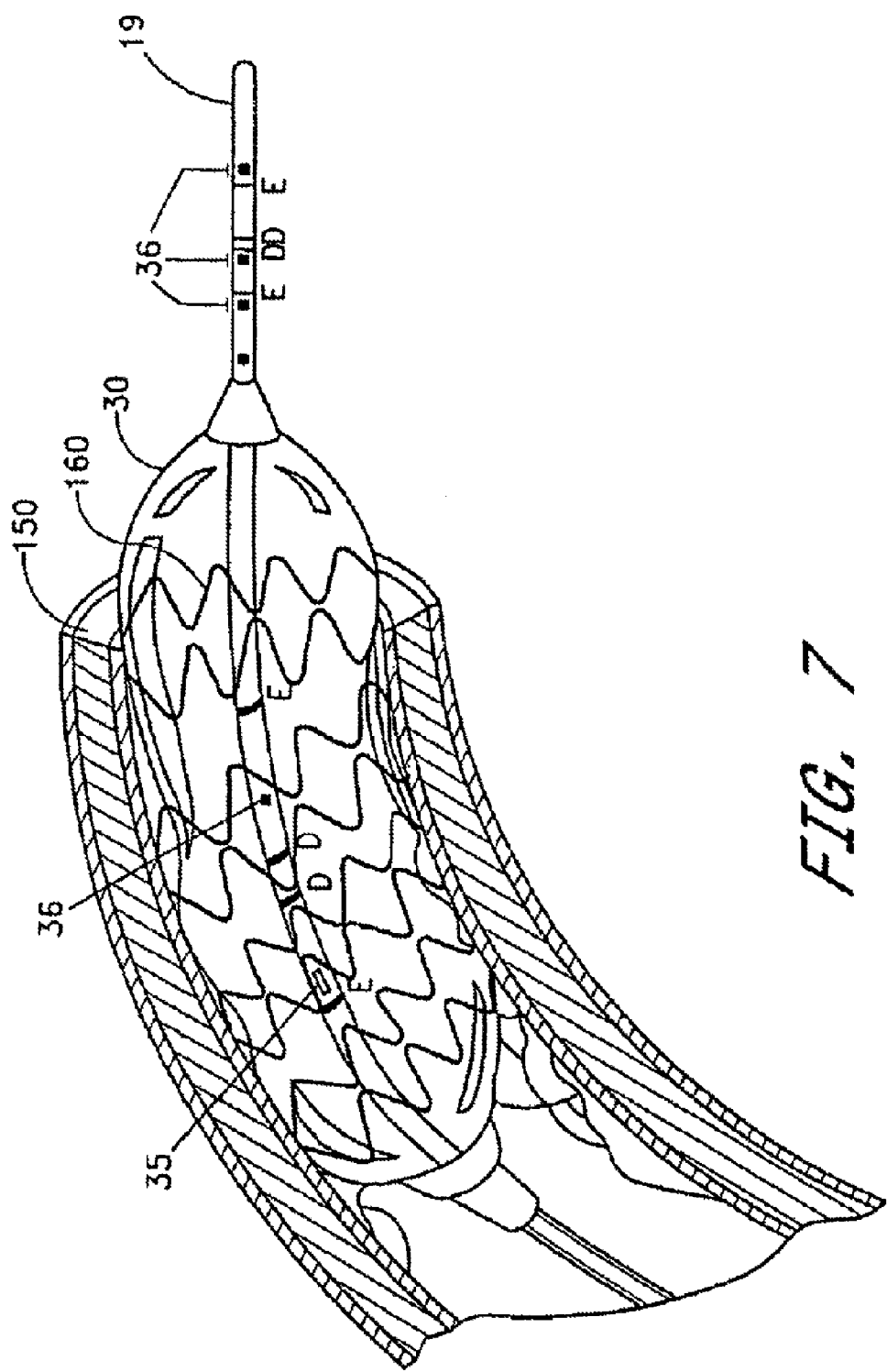
FIG. 7 illustrates balloon distension of a stent into the lumen of the coronary artery.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stenosis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and devices described herein can be applied to any body lumen or treatment site. For example, the methods, systems, and devices described herein can be applied to any one of the following exemplary bodily hollow systems: the cardiovascular system including the heart; the digestive system; the respiratory system; the reproductive system; and the urogenital tract.

Finite Element Analysis: In one preferred approach, finite element analysis (FEA) is used to verify the validity of Equations [4] and [5]. There are two major considerations for the model definition: geometry and electrical properties. The general equation governing the electric scalar potential distribution, V, is given by Poisson's equation as:

$$\nabla \cdot (C \nabla V) = -I \quad [24]$$

where C, I, and $\nabla$ are the conductivity, the driving current density, and the del operator, respectively. Femlab or any standard finite element packages can be used to compute the nodal voltages using Equation [24]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel, % I, can be used as an index of both leakage and field homogeneity. Hence, the various geometric and electrical material properties can be varied to obtain the optimum design; i.e., minimize the non-homogeneity of the field. Furthermore, the experimental procedure was simulated by injection of the two solutions of NaCl to verify the accuracy of Equation [4]. Finally, an assessment of the effect of presence of electrodes and catheter in the lumen of vessel may be performed. The error terms representing the changes in measured conductance due to the attraction of the field to the electrodes and the repulsion of the field from the resistive catheter body were quantified.

Poisson's equation for the potential field was solved, taking into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Theoretically, it is impossible to ensure a completely homogeneous field given the current leakage through the vessel wall into the surrounding tissue. Research leading to the disclosure of the present application identified that the isopotential line is not constant as one moves out radially along the vessel as stipulated by the cylindrical model. In one embodiment, a catheter with a radius of 0.55 mm is considered whose detected voltage is shown in FIGS. 8A and 8B for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5, and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, the simulation generates the "hill" whose value corresponds to the equivalent potential in the vessel as used in Eq. [4]. Hence, for each catheter size, the dimension of the vessel was varied such that equation [4] is exactly satisfied. Consequently, the optimum catheter size for a given vessel diameter was obtained such that the distributive model satisfies the lumped equations (Equation [4] and [5]). In this way, a relationship between vessel diameter and catheter diameter may be generated such that the error in the CSA measurement is less than 5%.

In an exemplary embodiment, different diameter catheters are prepackaged and labeled for optimal use in certain size vessel. For example, for vessel dimension in the range of 4-5 mm, 5-7 mm or 7-10 mm, analysis in accordance with the disclosure of the present application shows that the optimum diameter catheters will be in the range of 0.9-1.4, 1.4-2.0 or 2.0-4.6 mm, respectively. A clinician can select the appropriate diameter catheter based on the estimated vessel diameter of interest. This decision will be made prior to the procedure and will serve to minimize the error in the determination of lumen CSA.

It can be appreciated that any number of devices may be used in accordance within the scope of the present disclosure, including, but not limited to, any number of catheters and/or wires. In exemplary embodiments, catheters, including, but not limited to, impedance and/or guide catheters, and wires, including, but not limited to, impedance wires, guide wires, pressure wires, and flow wires, may be used as appropriate as devices, systems, and/or portions of systems of the present disclosure, and may be used as appropriate to perform one or more methods, or steps thereof, of the present disclosure.

While various embodiments of systems and methods for determining a phasic change in a vessel and vessel compliance have been described in considerable detail herein, the embodiments are merely offered by way of non-limiting examples of the disclosure described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

I claim:

1. A method for determining vessel compliance, the method comprising the steps of:
   introducing a device into a site within a vessel, the device comprising:
      a pair of excitation electrodes positioned along a portion of the device; and
      a pair of detection electrodes positioned along a portion of the device, the pair of detection electrodes comprising two detection electrodes having a known distance from one another, the pair of detection electrodes physically positioned in between the pair of excitation electrodes;
   operating the device in connection with two or more fluid injections in the vessel at or near the site to obtain two or more conductance values, each of the two or more fluid injections having a known conductivity;
   calculating a first vessel parameter of the site based on at least two of the two or more conductance values and the conductivities of at least two of the two or more fluid injections;
   calculating a second vessel parameter of the site based on at least two of the two or more conductance values and the conductivities of at least two of the two or more fluid injections;
   calculating a change in vessel parameter based upon the first vessel parameter and the second vessel parameter;
   calculating vessel compliance based upon the relationship between the change in vessel parameter and a change in pressure during a cardiac cycle; and
   calculating an index of compliance based in part upon a difference between the first vessel parameter and the second vessel parameter divided by the first vessel parameter.

2. The method of claim 1, further comprising the step of:
   determining the extent of vessel disease based upon the calculated vessel compliance.

3. The method of claim 2, wherein the extent of vessel disease is determined to be relatively low if the calculated vessel compliance is relatively high.

4. The method of claim 2, wherein the extent of vessel disease is determined to be relatively high if the calculated vessel compliance is relatively low.

5. The method of claim 2, wherein the extent of vessel disease is determined to include vessel calcification if the calculated vessel compliance is zero.

6. The method of claim 2, wherein the extent of vessel disease includes a vessel disease selected from the group consisting of atherosclerosis, vessel calcification, degenerative calcific disease, congenital heart disease, rheumatic disease, and coronary artery disease.

7. The method of claim 1, wherein the two or more conductance values are retrieved by a data acquisition and processing system operably connected to the device, and wherein the data acquisition and processing system is operable to calculate vessel compliance.

8. The method of claim 1, wherein the change in pressure during a cardiac cycle has a constant value for a patient.

9. The method of claim 1, wherein the first vessel parameter and the second vessel parameter each comprise a vessel diameter, and wherein the change in vessel parameter comprises a change in vessel diameter.

10. The method of claim 1, wherein the first vessel parameter and the second vessel parameter each comprise a vessel cross-sectional area, and wherein the change in vessel parameter comprises a change in vessel cross-sectional area.

11. The method of claim 1, wherein the first vessel parameter comprises a first vessel systolic diameter, wherein the second vessel parameter comprises a second vessel diastolic diameter, and wherein the first vessel systolic diameter and the second vessel diastolic diameter are representative of a single vessel.

12. The method of claim 1, wherein the first vessel parameter comprises a first vessel systolic cross-sectional area, wherein the second vessel parameter comprises a second vessel diastolic cross-sectional area, and wherein the first vessel systolic cross-sectional area and the second vessel diastolic cross-sectional area are representative of a single vessel.

13. The method of claim 1, wherein the device comprises a device selected from the group consisting of an impedance catheter, a guide catheter, a guide wire, and a pressure wire.

14. The method of claim 1, wherein the device further comprises an inflatable balloon positioned along a portion of the device, and wherein the method further comprises the step of inflating the balloon to breakup materials causing stenosis at the site.

15. The method of claim 14, wherein the device further comprises a stent positioned over the balloon, the stent capable of being distended to a desired size and implanted into the site, and wherein the method further comprises the steps of:
   distending the stent by inflating the balloon; and
   releasing and implanting the stent into the site.

16. The method of claim 15, wherein the balloon is inflated using a fluid, and wherein the method further comprises the steps of:
   providing electrical current to the fluid filling the balloon at various degrees of balloon distension;
   measuring a conductance of the fluid inside the balloon; and
   calculating a cross-sectional area of the balloon lumen.

17. The method of claim 1, wherein the device comprises at least one suction/infusion port in communication with at least one lumen of the device, whereby the two or more fluid injections occur via the at least one suction/infusion port.

18. A method for determining vessel compliance, the method comprising the steps of:
   introducing a device into a site within a vessel, the device comprising a pair of excitation electrodes and a pair of detection electrodes positioned therebetween;
   operating the device to obtain two or more conductance values;
   calculating a change in cross-sectional area based in part upon the two or more conductance values;
   calculating vessel compliance based upon the relationship between the change in cross-sectional area and a change in pressure during a cardiac cycle; and
   calculating an index of compliance based in part upon a difference between the first vessel parameter and the second vessel parameter divided by the first vessel parameter.

19. A system for determining vessel compliance, the system comprising:
   a device capable of acquiring conductance data, the device comprising:
      a pair of excitation electrodes positioned along a portion of the device; and
      a pair of detection electrodes positioned along a portion of the device, the pair of detection electrodes comprising two detection electrodes having a known distance from one another, the pair of detection electrodes physically positioned in between the pair of excitation electrodes along a portion of the device;
   an injection source for injecting one or more solutions through the device to a target site;
   a current source for providing current to the device; and
   a data acquisition and processing system that receives conductance data from the device, wherein the data acquisition and processing system is operable to calculate vessel compliance based upon:
      a. a calculated change in vessel parameter based upon a calculated first vessel parameter and a calculated second vessel parameter, the calculated first vessel parameter and a calculated second vessel parameter calculated based upon the conductance data acquired from the device; and
      b. a calculated relationship between the calculated change in vessel parameter and a change in pressure during a cardiac cycle;
   wherein the data acquisition and processing system is further operable to calculate an index of compliance based in part upon a difference between the first vessel parameter and the second vessel parameter divided by the first vessel parameter.

* * * * *